United States Patent [19]

Finch

[11] 4,036,965

[45] July 19, 1977

[54] 5-SULFINYL-2-PYRIDINECARBOXYLIC ACIDS

[75] Inventor: Neville Finch, West Orange, N.J.

[73] Assignee: Ciba-Geigy Corporation, Ardsley, N.Y.

[21] Appl. No.: 663,939

[22] Filed: Mar. 4, 1976

[51] Int. Cl.$^2$ .................. A61K 31/455; C07D 213/32
[52] U.S. Cl. .................. 424/266; 260/294.8 R; 260/294.8 G; 260/294.9
[58] Field of Search .............. 424/266; 260/294.8 R, 260/294.86, 294.9

[56] References Cited

U.S. PATENT DOCUMENTS

| 3,663,700 | 5/1972 | Umezawa et al. | 424/266 |
| 3,712,900 | 1/1973 | Thiele et al. | 424/266 |
| 3,862,159 | 1/1975 | Umezawa et al. | 424/266 |
| 3,914,239 | 10/1975 | Kuhnis et al. | 424/266 |
| 3,935,221 | 1/1976 | Miyano et al. | 424/266 |

*Primary Examiner*—Norman A. Drezin
*Attorney, Agent, or Firm*—Joseph G. Kolodny; Theodore O. Groeger; John J. Maitner

[57] ABSTRACT

5-Sulfinyl-2-pyridinecarboxylic acids, e.g. those of the formula

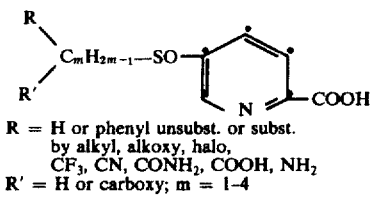

R = H or phenyl unsubst. or subst.
by alkyl, alkoxy, halo,
$CF_3$, CN, $CONH_2$, COOH, $NH_2$
R' = H or carboxy; m = 1–4 or functional derivatives thereof, are hypotensive agents.

8 Claims, No Drawings

5-SULFINYL-2-PYRIDINECARBOXYLIC ACIDS

BACKGROUND OF THE INVENTION

Fusaric acid, i.e. 4-butyl-2-pyridinecarboxylic acid, the 3- and/or 6-(alkoxy, amino, halo or hydroxy)-derivatives thereof or halofusaric amides of U.S. Pat. Nos. 3,914,239 or 3,935,221, are known antihypertensive agents, by virtue of their vasodilating and dopamine-$\beta$-hydroxylase inhibitory action, but they also produce tachycardia. Surprisingly, it was found that 2-pyridinecarboxylic acids having a specially substituted sulfinyl group in the 5-position, instead of an alkyl, haloalkyl, alkoxy or cycloalkoxy group therein, are not dopamine-$\beta$-hydroxylase inhibitors, and produce less tachycardia. Therefore, they are valuable hypotensive agents with minimal cardiac and other side-effects.

SUMMARY OF THE INVENTION

The present invention concerns and has for its object the provision of new 5-sulfinyl-2-pyridinecarboxylic acids and functional derivatives thereof, more particularly of those corresponding to Formula I

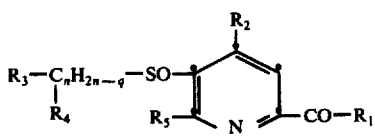

(I)

wherein $R_1$ is hydroxy, lower alkoxy, amino, mono- or di-lower alkylamino or hydrazino, $R_2$ is hydrogen, lower alkyl, lower alkoxy or halo, $R_3$ is hydrogen, lower alkoxy, lower alkylsuflinyl, halogeno, amino, mono- or di-lower alkylamino, phenyl or phenyl substituted by one or more than one member selected from lower alkyl, lower alkoxy, halo, trifluoromethyl, cyano, $COR_1$ or amino, $R_4$ is hydrogen, hydroxy or $COR_1$, $R_5$ is hydrogen, lower alkyl, lower alkoxy, halo or $COR_1$, $n$ is an integer from 1 to 7, $q$ is 1 or 3, $(n-q)$ is positive and in which 5-substituent all heteroatoms and double bonds are separated from each other by at least two carbon atoms, or a therapeutically useful salt thereof, as well as of corresponding pharmaceutical compositions and of methods of the preparation and application of said products, which are useful hypotensive agents in the treatment or management of hypertension in mammals.

DESCRIPTION OF THE PREFERRED EMBODIMENTS

A lower alkoxy group $R_1$, $R_2$, $R_3$, $R_5$, or within $R_3$ = (alkoxy)-phenyl is preferably methoxy, but also ethoxy, n- or i-propoxy or -butoxy; and such alkylsulfinyl group $R_3$ is preferably methyl- or ethylsulfinyl. The lower alkyl groups $R_2$ and $R_5$, or those within $R_1$ = alkylamino or $R_3$ = alkylphenyl, preferably represent methyl, but also ethyl, n- or i-propyl or -butyl. A halogen atom $R_2$, $R_3$, $R_5$, or within $R_3$ = halophenyl, is preferably fluoro, chloro or bromo. Accordingly, mono- or di-lower alkylamino groups $R_1$ or $R_3$ represent preferably mono- or di-(methylamino, ethylamino, n- or i-propylamino). A substituted phenyl radical $R_3$ contains preferably up to three, advantageously one or two of said members, such as methyl or ethyl; methoxy or ethoxy; fluoro, chloro or bromo; trifluoromethyl; amino; or said free, esterified or amidized carboxy groups. The term "lower" referred to above or hereinafter in connection with organic radicals or compounds respectively, defines such with up to 7, preferably up to 4, advantageously with one or two carbon atoms.

In the radical $R_3$, $R_4-C_nH_{2n-q}$, $R_4$ is preferably hydrogen, $n$ is preferably an integer from 1 to 4, and $q$ is 1, thus $C_nH_{2n-q}$ becomes methylene, 1,1- or 1,2-ethylene, 1,1-, 1,2- or 1,3-propylene, 1,1-, 1,2-, 1,3-, 1,4- or 2,3-butylene; provided it separates heteroatoms within $R_3$ from S by at least 2 carbon atoms. In case $q$ is 3, said radical represent preferably 1,3-prop-1-enylene, 1,3-but-1-enylene or 1,4-but-1 or 2-enylene.

The salts of the compounds of Formula I are preferably therapeutically acceptable alkali metal, e.g. sodium or potassium, salts of the free acids, or acid addition salts of the bases, e.g. those derived from the acids listed below.

The compounds of the invention exhibit valuable pharmacological properties, primarily hypotensive and antihypertensive activity. This is demonstrable in animal tests, using advantageously mammals, e.g. rats, cats or dogs, as test objects. The animals may either be normotensive or hypertensive, e.g. genetically or renal hypertensive rats or dogs. Said compounds can be applied to them enterally or parenterally, advantageously orally, subcutaneously, intravenously, intraperitoneally or intraduodenally, for example within gelatin capsules or in the form of starchy suspensions or aqueous solutions respectively. The applied dosage may range between about 0.1 and 200 mg/kg/day, preferably between about 1 and 100 mg/kg/day, advantageously between about 5 and 50 mg/kg/day. The lowering effect on the blood pressure is recorded either directly by means of a catheter, e.g. placed in the rat's caudal or dog's femoral artery, and a transducer, expressing the blood pressure prior and after dosing in mm/Hg, or indirectly by sphygmomanometry, e.g. at the rat's tail. Thus, for example, the 5-(m-chlorobenzylsulfinyl)-pyridine-2-carboxylic acid, or the 5-(m-trifluoromethylbenzylsulfinyl)-pyridine-2-carboxylic acid, two representative members of the compounds of the invention, are very effective in said tests, the latter is even slowing the heart rate. Accordingly, the compounds of the invention are useful antihypertensive agents in the treatment or management of essential or renal hypertension in mammals. They are also useful intermediates in the preparation of other valuable products, especially of pharmacologically active compositions.

Particularly useful are compounds of Formula I, in which $R_1$ is hydroxy, lower alkoxy, amino, mono- or di-lower alkylamino or hydrazino, each of $R_2$ and $R_5$ is hydrogen, lower alkyl, lower alkoxy or halogeno, $R_3$ is hydrogen, lower alkoxy, lower alkylsulfinyl, halogeno, di-lower alkylamino, phenyl or phenyl substituted by up to two members selected from lower alkyl, lower alkoxy, halo, trifluoromethyl, cyano, $COR_1$ or amino, $R_4$ is hydrogen, hydroxy or $COR_1$, $n$ is an integer from 1 to 7, $q$ is 1 or 3, $(n-q)$ is positive and in which 5-substituent all heteroatoms and double bonds are separated from each other by at least two carbon atoms, or a therapeutically useful ammonium, alkali metal or acid addition salt thereof.

Outstanding compounds of the invention are those of Formula II

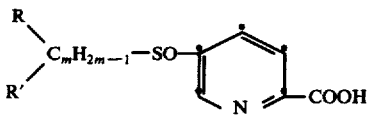

(II)

wherein R is hydrogen, phenyl or phenyl substituted by up to 2 members selected from lower alkyl, lower alkoxy, halo, trifluoromethyl, cyano, carboxy or amino, R' is hydrogen or carboxy and m is an integer from 1 to 4, or a therapeutically useful ammonium, alkali metal or acid addition salt thereof.

Most preferred are the compounds of Formula II, wherein R is phenyl, tolyl, anisyl, mono- or di-(fluoro or chloro)-phenyl, bromophenyl, trifluoromethylphenyl or cyanophenyl, R' is hydrogen and m is an integer from 1 to 4 or a therapeutically useful ammonium, alkali metal or acid addition salt thereof.

The compounds of the invention are prepared according to methods known per se, advantageously by:

1. hydrolyzing the nitrile of Formula III

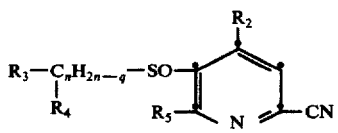

(III)

to the corresponding acid or amide and, if desired, converting any resulting compound into another compound of the invention. Said hydrolysis is performed according to known methods, preferably with aqueous acids or bases, such as strong mineral or carboxylic acids, or alkali metal hydroxides respectively, e.g. hydrochloric sulfuric, perchloric or acetic acid; sodium or potassium hydroxide, advantageously in the presence of lower alkanols. e.g. methanol or ethanol.

Another process for preparing the compounds of Formula I consists in:

2. oxidizing the sulfide of Formula IV

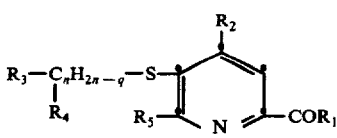

(IV)

to the corresponding sulfoxide and, if desired, converting any resulting compound into another compound of the invention. Said oxidation is also performed according to standard oxidation methods, advantageously with the use of mild oxidation agents or an equivalent amount of stronger oxidants, e.g. hydrogen peroxide or nitric oxides, oxidizing acids or their salts, such as periodic acid or suitable salts thereof, e.g. sodium periodate; m-chloro-perbenzoic acid; heavy metal salts or oxides, such as alkali metal chromates or permanganates, chromic or cupric salts, e.g. halides or sulfates thereof, or silver, mercuric, chromium VI or manganese IV oxide, in acidic or alkaline media respectively. In such oxidations, the conditions and starting materials are so chosen that no other oxidations will occur within the molecule, e.g. a hydroxy group $R_4$ oxidized to oxo or a double bond ($q=3$) epoxidized, unless it is desired that such unsaturated compound is converted via the epoxide or other derivative into another compound of the invention as described below. Otherwise, said hydroxy group may be protected during oxidation, for example, by acylation with a lower alkanoic acid halide or anhydride, and the oxidized acyl-derivative hydrolyzed with aqueous alkali metal hydroxides.

The compounds of the invention so obtained can be converted into each other according to known methods. For example, resulting free acids can be esterified with lower alkanols in the presence of said strong acids, or with diazo-lower alkanes, or converted into their halides by treatment with thionyl halides, or phosphorus halides or oxyhalides. Resulting esters may be hydrolyzed or transesterified in the presence of said alkaline or acidic agents respectively, or said esters or halides treated with ammonia, mono- or di-lower alkylamines or hydrazine, in order to obtain the amides or hydrazides. These, in turn, can be hydrolyzed or alcoholized under acidic or alkaline conditions. Resulting unsaturated compounds ($q = 3$ and $R_4 = H$) can be hydrohalogenated, hydrated or halogenated and any resulting mono- or bishalide treated with alkali metal lower alkoxides ammonia, mono- or di-lower alkylamines and/or alkali metal hydroxides, in order to obtain compounds with $R_3$ being lower alkoxy, amino, mono- or di-lower alkylamino and $R_4$ being hydrogen or hydroxy.

Finally, a resulting acid can be converted into its salts according to conventional methods, for example, by reacting it with a stoichiometric amount of a suitable salt-forming reagent, such as ammonia or an alkali metal hydroxide, carbonate or hydrogen carbonate. A salt of this type can be reconverted into the free acid by treatment with an acid, e.g. hydrochloric, sulfuric or acetic acid, until the proper pH has been reached. A resulting basic compound can be converted into a corresponding acid addition salt, for example, by reacting it with an inorganic or organic acid, preferably a therapeutically useful acid, or with a corresponding anion exchange preparation, and isolating the desired salt. An acid addition salt may be converted into the free compound by treatment with a base, e.g. a metal hydroxide, ammonia or a hydroxylion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, pamoic, nicotinic, methanesulfonic, ethanesulfonic, hydroxyethanesulfonic, ethylenesulfonic, benzenesulfonic, halobenzenesulfonic, toluenesulfonic, npahthalenesulfonic, sulfanilic or cyclohexylsulfamic acid.

These or other salts, for example, the picrates, can also be used for purification of the bases obtained; and bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-camphor sulfonates or d-$\alpha$-(1-naphthyl)-ethylamine or l-cinchonidine salts.

The above reactions are carried out according to standard methods, in the presence or absence of diluents, preferably such as are inert to the reagents and are solvents thereof, of catalyst, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. In the process of the invention, those starting materials are advantageously selected, which yield the above-described preferred embodiments thereof, especially those corresponding to Formula II.

The starting material used is known or, if new, may be prepared according to methods described for known analogs thereof and those illustrated by the examples herein. Thus, for example, the nitriles III are obtained from corresponding 2-methyl-5-mercapto-pyridines, which are oxidized with said peracids to give the corresponding 2-methyl-5-sulfoxide. The latter is reacted with potassium tert. butoxide and amyl nitrite, to yield the oxime of the corresponding 5-sulfinylpyridine-2-carboxaldehyde. The latter is dehydrated with methanesulfonyl chloride or acetic anhydride, to yield the nitriles of Formula III.

The sulfides IV are obtained according to the following steps: 5-amino-2-pyridinecarboxylic acid esters are dizaotized, the diazonium salt reacted with potassium and cuprous thiocyanate, followed by reducing the resulting 5-thiocyanate with sodium borohydride. The resulting 5-mercapto-2-pyridinecarboxylic acid esters are then reacted with compounds of the Formula V, $R_3$, $R_4$—$C_nH_{2n-q}$—Y(V) wherein Y is a hydroxy group esterified with a strong, inorganic or organic acid, preferably a hydrohalic, e.g. hydrochloric, - bromic or -iodic acid, or an alkane or benzene sulfonic acid, e.g. methane, p-toluene or m-bromobenzene sulfonic acid. Said condensation is carried out either in the presence of basic condensation agents, such as alkali metal or alkaline earth metal hydrides, hydroxides, carbonates or bicarbonates or organic nitrogen bases, e.g. tri-lower alkylamines, pyridines or quinolines; or preferably with alkali metal salts of said mercaptans in aprotic solvents, e.g. dimethylformamide of -sulfoxide. Also compounds V, wherein Y is metallized mercapto, can be reacted with 5-nitro-2-pyridinecarboxylic acid esters.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, callulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preservng, stabilizing, wetting or emulsifying agents, solution promotors, salts, for regulating the osmotic pressure and/or buffers. They may also contain other therapeutically valuable substances. Said pharmaceutical compositions are prepared according to conventional mixing, granulating or coating methods respectively and contain about 0.1 to 75% preferably about 1 to 50% of the active ingredient.

The following examples illustrating the invention, are not to be construed as being limitations thereon. Temperatures are given in degrees Centrigrade, all parts wherever given are parts by weight and, if not otherwise stated, all evaporations are carried out under reduced pressure, e.g. between about 0.1 and 15 mmHg.

EXAMPLE 1

The solution of 2.3 g of 5-n-butylsulfinyl-2-pyridinecarbonitrile in 15 ml of 20% potassium hydroxide and 15 ml of methanol is refluxed for 1 hour. Then the solution is cooled and the methanol is distilled off under reduced pressure. The residual aqueous layer is washed once with ether, and then the pH of the aqueous layer is adjusted to 6–7 with hydrochloric acid. It is extracted three times with ether, the extracts are combined, the combined ethereal solution is washed with water, dried, filtered and the filtrate evaporated. The residue is recrystallized from ethanol to yield 5-n-butylsulfinyl-2-pyridinecarboxylic acid; its sodium salt melts above 340° with decomposition.

The starting material is prepared as follows:

15.8 g of pyridine are added to an ethereal solution of one equivalent of methyl lithium, while stirring and maintaining a nitrogen atmosphere. The mixture is stirred for 16 hours at room temperature and then a solution of 13.5 g of n-butyldisulfide in 100 ml of tetrahydrofuran is added dropwise to the mixture. Then it is stirred for 6 hours at room temperature. The mixture is diluted with a mixture of ether plus water and the organic phase separated. The organic layer is washed with a saturated solution of potassium chloride, dried over anhydrous magnesium sulfate, filtered and the filtrate evaporated to an oil. This oil is dissolved in ether and the ethereal solution extracted twice with 4N-sulfuric acid. The aqueous acidic layer is separated, cooled in ice, is made basic and the basic solution is extracted twice with ether. The ethereal extracts are combined, the combined ethereal solution is washed with water, dried, filtered and the filtrate evaporated to an oil. This oil is distilled to yield 5-n-butylmercapto-2-methyl-pyridine boiling at 77°–91°/0.1 mmHg.

The solution of 10.8 g of the above distillate in 80 ml of tetrahydrofuran is added to a 0.5 M aqueous solution of sodium periodate, with stirring. The solution is stirred at room temperature for 16 hours and then evaporated to give a semi-solid residue. The residue is dissolved in a mixture of ether plus water, the layers are separated and the aqueous layer extracted three times with ether. The ethereal layer is combined with the ether extracts, and the resulting ethereal solution is washed with a saturated solution of potassium chloride. The ethereal solution is dried over anhydrous magnesium sulfate, filtered and the filtrate evaporated to give 5-n-butylsulfinyl-2-methyl-pyridine.

The solution of 7.5 g thereof in 60 ml of tetrahydrofuran is added to a solution of 14.0 g of potassium tertiary butoxide in tetrahydrofuran, while stirring and maintaining a nitrogen atmosphere. The solution is stirred for 2 hours at room temperature, cooled to 5° in an ice bath and then a solution of 14.6 g of isoamyl nitrite in 30 ml of tetrahydrofuran is added to the solution all in one portion. The temperature of the solution is allowed to rise to room temperature and the solution is additionally stirred at room temperature for 16 hours. After that, the solution is evaporated and the residue is dissolved in a mixture of ether plus water. The ethereal layer is separated and the aqueous layer is extracted once with ether. The aqueous layer is acidified to a pH of 2, extracted with ether and then the pH of the aqueous solution is adjusted to 6.8-7. The aqueous solution is saturated with sodium chloride and the saturated solution is extracted three times with ether. The ether extracts are combined, washed and dried over anhydrous magnesium sulfate. The ether solution is filtered and the filtrate evaporated to yield a solid. This solid is recrystallized from ether to give the oxime of 5-n-butylsulfinyl-2-pyridinecarboxaldehyde melting at 90°-91°.

To a stirred ice bath cold solution of 12.0 g of the above oxime in 80 ml of pyridine is added 7.3 g of methanesulfonyl chloride all in one portion. Then the mixture is additionally stirred for 2 hours at the ice bath temperature, the temperature is allowed to rise to room temperature and the mixture is further stirred for 14 hours at room temperature. The mixture is evaporated and the residue is suspended in water, the aqueous suspension is basified with potassium bicarbonate and then extracted four times with ether. The ether extracts are combined, washed with a saturated solution of potassium chloride and then dried over anhydrous magnesium sulfate. The ethereal solution is filtered and the filtrate evaporated to an oil. This oil is crystallized from isopropanol to give 5-n-butylsulfinyl-2-pyridinecarbonitrile melting at 54°-55°.

EXAMPLE 2

To the stirred solution of 10.28 g of 5-(m-chloro-benzylmercapto)-2-pyridinecarboxylic acid methyl ester in 150 ml of methylene chloride, cooled in an ice bath, 7.5 g of m-chloroperbenzoic acid are added in small portions during 10 minutes. The mixture is stirred for 3 hours, washed twice with 10% aqueous potassium bicarbonate, dried and evaporated. The residue is recrystallized from ethanol, to yield the 5-(m-chlorobenzylsulfinyl)-2-pyridinecarboxylic acid methyl ester of the formula

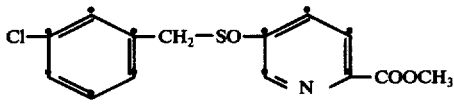

melting at 143°-144°.

The starting material is prepared as follows:

To the stirred suspension of 1.73 g of sodium hydride in 30 ml of dimethylformamide the solution of 12.7 g of m-chlorobenzylmercaptan is added during 2 minutes and stirring is continued for 15 minutes. Thereupon the solution of 12.25 g of 5-nitro-pyridine-2-carboxylic acid methyl ester in 75 ml of dimethylformamide is added all at once. The mixture is stirred for 1 hour on the steam bath and allowed to stand at room temperature overnight. It is poured onto ice and acetic acid, the suspension obtained filtered and the residue recrystallized from 95% aqueous ethanol, to yield the 5-(m-chlorobenzylmercapto)-2-pyridinecarboxylic acid methyl ester melting at 75°-77°.

The mixture of 250 g of m-chlorobenzyl chloride, 16.6 g of potassium thiocyanate and 150 ml of 95% aqueous ethanol is refluxed for 3 hours and evaporated. The residue is taken up in methylene chloride and water, the organic solution separated; washed with water dried and evaporated to yield the m-chlorobenzyl-thiocyanate.

The solution of 27.1 g thereof in the minimum amount of diethyl ether is added dropwise to the suspension of 6.7 g lithium aluminumhydride in 50 ml of diethyl ether while stirring and the mixture is refluxed for 90 minutes. The excess reagent is destroyed with saturated aqueous potassium sodium tartrate, the mixture filtered and the filtrate washed with water. It is dried and evaporated, to yield the m-chlorobenzylmercaptan. Analogously the m-trifluoromethylbenzylmercaptan is prepared.

EXAMPLE 3

To the stirred mixture of 9 g of 5-(m-chlorobenzylsulfinyl)-2-pyridinecarboxylic acid methyl ester and 40 ml of N aqueous sodium hydroxide methanol is added until dissolution occurs. The solution is heated at the steam bath for 10 minutes and stirred overnight at room temperature. It is evaporated, the residue taken up in the minimum amount of hot water, the solution filtered, the filtrate cooled and the precipitate formed collected, to yield the sodium 5-(m-chlorobenzylsulfinyl)-2-pyridinecarboxylate.

It is dissolved in warm water, the solution acidified with 20 ml of N hydrochloric acid and the precipitate formed collected, to yield the corresponding acid melting at 168°-170°.

EXAMPLE 4

Analogous to the methods illustrated by Examples 2 and 3, and the 6-methyl-5-(m-trifluoromethylbenzylsulfinyl)-pyridine-2-carboxylic acid is prepared, melting at 170°-172°.

The starting material is prepared as follows:

To the stirred suspension of 1.08 g of sodium hydride in 25 ml of dimethylformamide the solution of 9.0 g of m-trifluoromethylbenzylmercaptan in 50 ml of dimethylformamide is added during 3 minutes and the mixture stirred for 10 minutes. It is combined with 7.75 g of 6-methyl-5-nitropyridine-2-carboxylic acid methyl ester and the whole stirred on the steam bath for 30 minutes and allowed to stand overnight at room temperature. 2 ml of acetic acid are added and the solution is mixed with ice water to produce a dense, grainy precipitate. It is filtered off and recrystallized from isopropanol-diethyl ether, to yield the 6-methyl-5-(m-trifluoromethylbenzylmercapto)-pyridine-2-carboxylic acid methyl ester melting at 91°-93°.

EXAMPLE 5

According to the methods of previous examples, advantageously Examples 2 and 3, the following compounds of Formula II are prepared from equivalent amounts of the corresponding starting materials: R' = H

| No. | R | $C_mH_{2m-1}$ | Salt | m.p.° C |
|---|---|---|---|---|
| 1 | phenyl | $CH-(CH_3)_2$ | Na | 290–300 |
| 2 | m-$CH_3O-C_6H_4$ | CH | — | 106–107 |
| 3 | p-$CH_3O-C_6H_4$ | " | — | 184–187 |
| 4 | m-Cl-$C_6H_4$ | " | — | 168–170 |
| 5 | p-Cl-$C_6H_4$ | " | — | 197–199 |
| 6 | o,o-$Cl_2-C_6H_3$ | " | — | 193–196 |
| 7 | o,p-$Cl_2-C_6H_3$ | " | Na | 320 dec. |
| 8 | m-Br-$C_6H_4$ | " | " | 270 dec. |
| 9 | m-$CF_3-C_6H_4$ | " | — | 170–175 |
| 10 | " | $C-CH_3$ | — | 150–152 |
| 11 | m-CN-$C_6H_4$ | CH | — | 193–195 |

Other starting materials may be prepared as follows:

To the solution of 28.3 g of 5-aminopyridine-2-carboxylic acid methyl ester in 80 ml of 20% sulfuric acid, cooled to −4°, the solution of 14.31 g of sodium nitrite in 30 ml of water is added dropwise while stirring and maintaining the temperature below 0°. Thereafter the mixture is stirred for 15 minutes below 0° and the mixture of 28 g of potassium thiocyanate and 8 g of cuprous thiocyanate is added portionwise to said solution. Each addition causes evolution of gas and a black oil to separate. With continued stirring the oil again dissolves and the solution is stirred for 3 hours. It is extracted with methylene chloride, the extract filtered and evaporated, to yield the 5-thiocyanatopyridine-2-carboxylic acid methyl ester.

To the solution of 25.2 g thereof in 250 ml of methanol 5 g of sodium borohydride are added in small portions during 15 minutes while maintaining the temperature from −7° to about 15°. After 10 minutes the mixture is evaporated, the residue taken up in 5% hydrochloric acid and methylene chloride, the organic phase washed with water, dried and evaporated, to give the 5-mercaptopyridine-2-carboxylic acid methyl ester.

EXAMPLE 6

Preparation of 10,000 tablets each containing 100 mg of the active ingredient:

| Formula: | |
|---|---|
| 5-(m-chlorobenzylsulfinyl)-pyridine-2-carboxylic acid | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Analogously tablets are prepared, which contain one of the remaining compounds of the previous examples.

EXAMPLE 7

To the stirred solution of 6.5 g of 5-n-butylmercaptopyridine-2-carboxylic acid methyl ester in 200 ml of methylene chloride, the solution of 5.7 g of m-chloroperbenzoic acid in 100 ml of methylene chloride is added during 15 minutes while cooling with ice. It is stirred another 15 minutes and allowed to stand at room temperature overnight. It is washed with 10% aqueous sodium bicarbonate and water, dried and evaporated. The residue is recrystallized from benzene-hexane (1:1), to yield the 5-n-butylsulfinylpyridine-2-carboxylic acid methyl ester melting at 150°–154°.

The stirred mixture of 5.1 g thereof, 4 ml of water, 20 ml of isopropanol and 1.7 g of 50% aqueous sodium hydroxide is heated on the steam bath for 1 hour. It is cooled, diluted with diethyl ether and the precipitate formed in the cold collected. It is dissolved in 5 ml of water and 10 ml of isopropanol, the mixture heated and filtered hot. The filtrate is diluted with isopropanol, cooled with ice and the precipitate collected, to yield the corresponding sodium salt melting above 340° with decomposition.

I claim:

1. A compound of the formula

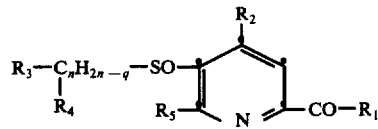

wherein $R_1$ is hydroxy, lower alkoxy, amino, mono- or di-lower alkylamino or hydrazino, $R_2$ is hydrogen, lower alkyl, lower alkoxy or halo, $R_3$ is hydrogen, lower alkoxy, lower alkylsulfinyl, halogeno, amino, mono- or di-lower alkylamino, phenyl or phenyl substituted by one or more than one member selected from the group consisting of lower alkyl, lower alkoxy, halo, trifluoromethyl, cyano, $COR_1$ and amino, $R_4$ is hydrogen, hydroxy or $COR_1$, $R_5$ is hydrogen, lower alkyl, lower alkoxy, halo or $COR_1$, $n$ is an integer from 1 to 7, $q$ is 1 and which $C_nH_{2n-q}$-moiety separates $R_3$ being lower alkoxy, lower alkyl-sulfinyl, halogeno, amino, mono- or di-lower alkylamino, and $R_4$ being hydroxy, from the SO-group by at least two carbon atoms, or a therapeutically useful salt thereof.

2. A compound as claimed in claim 1, in which formula $R_1$ is hydroxy, lower alkoxy, amino, mono- or di-lower alkylamino or hydrazino, each of $R_2$ and $R_5$ is hydrogen, lower alkyl, lower alkoxy or halogeno, $R_3$ is hydrogen, lower alkoxy, lower alkylsulfinyl, halogeno, di-lower alkylamino, phenyl or phenyl substituted by up to two members selected from the group consisting of lower alkyl, lower alkoxy, halo, trifluoromethyl, cyano, $COR_1$ and amino, $R_4$ is hydrogen, hydroxy or $COR_1$, $n$ is an integer from 1 to 7, $q$ is 1 and which $C_nH_{2n-q}$-moiety separates $R_3$ being lower alkoxy, lower alkylsulfinyl, halogeno, amino, mono- or di-lower alkylamino, and $R_4$ being hydroxy, from the SO-group by at least two carbon atoms, or a therapeutically useful ammonium, alkali metal or acid addition salt thereof.

3. A compound as claimed in claim 1 and corresponding to the formula

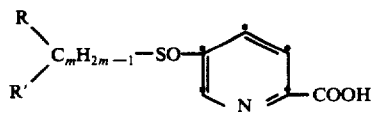

wherein R is hydrogen, phenyl or phenyl substituted by up to 2 members selected from the group consisting of lower alkyl, lower alkoxy, halo, trifluoromethyl, cyano, carboxy and amino, R' is hydrogen or carboxy and $m$ is an integer from 1 to 4, or a therapeutically useful ammonium, alkali metal or acid addition salt thereof.

4. A compound as claimed in claim 3, in which formula R is phenyl, tolyl, anisyl, mono- or di-(fluoro or chloro)-phenyl, bromophenyl, trifluoromethylphenyl or cyanophenyl, R' is hydrogen and $m$ is an integer from 1 to 4 or a therapeutically useful ammonium, alkali metal or acid addition salt thereof.

5. A compound as claimed in claim 3 and being the 5-(m-chlorobenzylsulfinyl)-pyridine-2-carboxylic acid.

6. A compound as claimed in claim 3 and being the 5-(m-trifluoromethylbenzylsulfinyl)-pyridine-2-carboxylic acid.

7. A hypotensive pharmaceutical composition comprising a hypotensively effective amount of a compound as claimed in claim 1, together with pharmaceutical excipient.

8. A method of lowering the blood pressure in a mammal suffering from hypertension, which comprises administering to said mammal enterally or parenterally a hypotensively effective amount of a composition as claimed in claim 7.

* * * * *